US009763439B2

(12) United States Patent
Junqueira Conceicao Gonsalves et al.

(10) Patent No.: US 9,763,439 B2
(45) Date of Patent: Sep. 19, 2017

(54) METHOD OF PACKAGING FOOD (71) Applicant: Universidad de Santiago de Chile, Santiago (CL)

(72) Inventors: Maria Paula Junqueira Conceicao Gonsalves, Santiago (CL); Andrea Marcarena Tapia Ulloa, Santiago (CL)

(73) Assignee: Universidad de Santiago de Chile, Santiago (CL)

( * ) Notice: Subject to any disclaimer, the term of this patent is extended or adjusted under 35 U.S.C. 154(b) by 0 days.

(21) Appl. No.: 15/243,648

(22) Filed: Aug. 22, 2016

(65) Prior Publication Data

US 2016/0353732 A1  Dec. 8, 2016

Related U.S. Application Data (60) Division of application No. 14/504,170, filed on Oct. 1, 2014, now abandoned, which is a continuation of application No. PCT/CL2013/000020, filed on Apr. 2, 2013.

(51) Int. Cl.

| | |
|---|---|
| *A01N 37/00* | (2006.01) |
| *A61K 31/19* | (2006.01) |
| *A01N 25/10* | (2006.01) |
| *A01N 25/34* | (2006.01) |
| *A01N 37/06* | (2006.01) |
| *B65B 55/00* | (2006.01) |
| *B65D 81/28* | (2006.01) |
| *B65D 85/34* | (2006.01) |
| *B29C 37/00* | (2006.01) |
| *B29C 47/00* | (2006.01) |
| *C08J 7/04* | (2006.01) |
| *C09D 5/14* | (2006.01) |
| *C09D 7/12* | (2006.01) |
| *C09D 183/04* | (2006.01) |
| *B29K 67/00* | (2006.01) |
| *B29K 105/26* | (2006.01) |
| *B29L 9/00* | (2006.01) |
| *B29L 31/00* | (2006.01) |
| *C08K 5/098* | (2006.01) |

(52) U.S. Cl.
CPC ............. *A01N 25/10* (2013.01); *A01N 25/34* (2013.01); *A01N 37/06* (2013.01); *B29C 37/0025* (2013.01); *B29C 47/0021* (2013.01); *B65B 55/00* (2013.01); *B65D 81/28* (2013.01); *B65D 85/34* (2013.01); *C08J 7/047* (2013.01); *C09D 5/14* (2013.01); *C09D 7/1233* (2013.01); *C09D 183/04* (2013.01); *B29K 2067/003* (2013.01); *B29K 2105/26* (2013.01); *B29K 2995/0037* (2013.01); *B29L 2009/005* (2013.01); *B29L 2031/712* (2013.01); *C08J 2367/02* (2013.01); *C08J 2483/04* (2013.01); *C08K 5/098* (2013.01)

(58) Field of Classification Search
CPC ........ A01N 37/06; A01N 25/10; A01N 25/34; C08J 2367/02; C08J 2483/04; C08J 7/047; C09D 183/04; C09D 5/14; C09D 7/1233

See application file for complete search history.

(56) References Cited

U.S. PATENT DOCUMENTS

| | | |
|---|---|---|
| 3,780,140 A | 12/1973 | Hammer |
| 5,980,826 A | 11/1999 | Barenberg et al. |
| 6,077,495 A | 6/2000 | Speronello et al. |
| 2015/0025144 A1 | 1/2015 | Junqueira Conceicao Gonsalves et al. |

FOREIGN PATENT DOCUMENTS

| | | |
|---|---|---|
| WO | WO 00-53413 | 9/2000 |
| WO | WO 2004-056214 | 7/2004 |
| WO | WO 2005-041660 | 5/2005 |

OTHER PUBLICATIONS

Vartiainen et al, Packaging Technology and Science, 2003; 16: 223-229.
Quintavalla, S. et al. "Antimicrobial food packaging in meat industry", Meat Science, 62 (2002) pp. 373-380.
International Search Report and Written Opinion for International Application No. PCT/USO4/34197, dated Feb. 2005.

*Primary Examiner* — Jean Cornet
(74) *Attorney, Agent, or Firm* — Bryan D. Zerhusen; Locke Lord LLP (57) ABSTRACT The invention proposes a container further extending the shelf life of foods, particularly berries, by including an active agent having antifungal capability into the container surface so that when the fruit is packaged inside the container it is permanently exerted an antifungal effect over the surface, which is the place on the longer determinants occurs, but also contributing to preserve the general environment. Also it proposes a preparation process and its use.

7 Claims, 9 Drawing Sheets

METHOD OF PACKAGING FOOD

CROSS-REFERENCE TO RELATED APPLICATIONS

This application is divisional application of U.S. Non-provisional application Ser. No. 14/504,170, filed 1 Oct. 2014, which is a continuation of International Application No. PCT/CL2013/000020 filed on Apr. 2, 2013, which claims priority to Chilean Application No. 814-2012 filed on Apr. 2, 2012, which applications are incorporated herein by reference.

TECHNICAL FIELD

The present invention concerns an eco-active packaging for elaborated foodstuff or fruits or fresh vegetables, its preparation process and its use.

RELATED ART

During recent years, there has been a continuing modernization of agricultural activity, focused on the increase of productivity and quality, which has allowed a continuous development and the capacity to adjust the offer to the evolution of consumer habits and preferences.

Within this context, there has been special interest in the incorporation of quality, food health and safety standards, the strengthening of local zoo and phyto-sanitary heritage, environmental concern, corporate social responsibility, technological innovation and market management. All of which are instruments that favor production differentiation.

Fresh exportable products present high perishability, which dramatically affects their quality when arriving to distant markets and thus reducing their value. Therefore, to extend their lifespan and to keep food safety an quality of fresh products to be exported is a constant challenge to the industry.

Basically, two problems must be faced when seeking to keep fruits and vegetables fresh. First, they are alive and many chemical and biochemical reactions are occurring. Some reactions, if not controlled, may rapidly lead to the aging of vegetables and the loss of freshness. Secondly, the risk of microbiological contamination must be delayed as long as possible, since it compromises food safety, as well as the product final quality. Microbiological growth may cause serious alterations such as smell, funny taste and/or alteration in color and texture of vegetables (King & Bolin, 1989).

Particularly, berries are highly perishable and present important after-harvest physiological activity. As a consequence, they have short ripening and aging periods, which makes their commercialization a real challenge. They're susceptible to develop after-harvest diseases, to the point that some symptoms can be observed only 12 hours after being kept at room temperature, specially if they are yet. In general, the lifespan of berries is limited due to diseases caused by fungi, particularly *Botrytis cinerea*.

Studies in USA show that annual loss of fresh berries through the commercialization chain can rise to a 40% of national production, which causes many millions of dollars in loss, even though that country is known for its high technology and for presenting different means for refrigerated transport.

*Botrytis cinerea* is the agent that causes the "gray rottenness", which infects more than 200 different vegetal species, producing serious economic loss before and after picking. This pathogen may attack the crop in any of its developing states and can infect any part of the plant. Due to the considerable impact of this pathogen and to the economic consequences on important crops such as grapes, tomatoes, strawberries, raspberries, cranberries, among others, there is an important number of studies on the biology of this fungus, the interactions in which it participates and on possible methods to control it (Benito et al., 2000).

Although berries may be of a high quality, they present a short lifespan, mainly because of fungal growth (*Botrytis*), which causes important loss due to product rejection and to the poor quality image in the target markets. On the other hand, berries are exported in packages not according to international market trends.

Considering international trends, it is essential, to develop recyclable and/or active biodegradable packaging with antimicrobial capacity, allowing to increase the lifespan of berries, as well as their quality and safety, at a competitive price, considering the packaging traditionally used by the industry nowadays. All this without significantly modifying the present packaging production line nor their common use form.

Controlling physiological processes and the growth of microorganism is the key to the preservation and long lifespan of fruits and vegetables. That way, packaging systems and low temperatures are technologies that contribute to the extension of lifespan, quality and safety of these products.

Packaging systems and low temperatures are technologies that contribute to the extension of lifespan, quality and safety of fresh fruits.

Fresh fruits are mostly exported using Modified Atmosphere Technology in order to reduce metabolic processes and bioburden. Usually, entire coverage for pallets is used to contain the modified atmosphere. These conditions, however, are complex in practice, expensive, and may be affected by external factors, such as blackouts or leaks, making often non-viable to maintain the process for periods over 30–35 days, in the case of blueberries. The main difficulty of this technology informed by some berry exporting companies is the variation in the gaseous mixtures in different pallets, making the homogenization of the exported load a difficult task.

At present, one of the main requirements in food industry is the development of non-invasive procedures that may cause a minimum alteration in food physicochemical and sensory characteristics. In this context, active packages arise as an excellent alternative to complement these requirements, since they expand the lifespan of food, minimize additive incorporation and improve food safety at a minimum alteration of its characteristics, providing the chance to develop new products. Beside, active packages can be combined with other technologies, adding a synergic effect, increasing the quality and lifespan of the product.

Not long ago, packaging had a merely passive function, which consisted in separating the product from the environment, acting as a shield against physical and/or mechanical effects, chemical reactions and the invasion of microorganisms, as well as preventing migration of their own compounds into food, with minimal interaction with the food, and therefore becoming an inert shield.

In the last few years, in the area of food packaging a dramatic step forward has occurred concerning new packaging techniques. From a traditional system, focused on the search of the maximum inertia between package and food, there has been a turn to the development of a kind o packaging called active packaging, being packages which interact with the food in order to improve its properties. Thus, active packaging can be defined as a system in which food, packaging and environment act positively to increase the lifespan or to improve some property of the food, which has eventually led to the concept of packaging as an emerging technology in food preservation (www.cyted.org).

However, during recent years, with the demand for fresh and better quality products, the concept of packaging has changed to offer an active protection to the product. Thus, active packaging can be defined as a system in which food, packaging and environment act positively to increase the lifespan or to improve some property of the food (Miltz et al., 1995).

The packaging can be called active when it performs a desired role, as well as providing an inert shield against external conditions. The word "desired" is important for this definition, because it makes clear difference between desired and non-desired effects (Rooney, 1995).

The most important active packaging conceptions are: antimicrobial packaging; edible covering; oxygen, ethylene, odors and taste absorbers; moisture regulators; carbon dioxide, antimicrobials, antioxidant and flavors releasers. Their applications are many and their use is clearly growing.

The active packaging system has been used for years in Japan and in recent years its use has been growing in Europe and the United States.

Consequently, active packaging technology is an emerging and promising area in food technology, which may contribute with several preservation benefits in a broad variety of products. The current concern as to how to improve and guarantee safety in processed food has raised great interest in the use of active antimicrobial packaging. Lately, the main teams worldwide on food packaging research along with leading companies in the development of packaging are doing an important effort to develop active packages with antimicrobial capacity.

Nevertheless, many patented developments are targeted to the use of compounds whose use in food packaging is conditioned, since the legislation in many countries forbids such compounds in direct contact with the food, as it is the case of silver ions, for instance.

Within the concept of active packaging, the antimicrobial packaging is defined as the packaging which incorporates active antimicrobial agents instead of the same substances added directly on the food. The concept of antimicrobial packaging assumes the gradual release of the antimicrobial agent from the packaging to the food, inhibiting or delaying microorganism growth on its surface (Appendini & Hotchkiss, 2002).

As the microbiological contamination of most food occurs mainly on the surface due to the processing and subsequent manipulation, efforts have been made to improve safety, delaying food deterioration through the use of antimicrobials applied with aerosols or by immersion. However, direct superficial application of antibacterial substances on food has limited benefits, since active substances are neutralized in contact, or are rapidly diffuse from the surface to the interior of food. On the other hand, incorporation of a bactericidal or bacteriostatic substance in food formulations may result in partial inactivation of the active substances by constituents of the product itself and a limited effect on the surface microflora can be expected (Quintavalla & Vicini, 2002).

Therefore, the use of active packaging which contains antimicrobial agents could be more efficient, due to the slow migration of agents from the packaging material to the surface of the product, helping to keep high concentrations where they are more necessary. If an antimicrobial agent can migrate from the packaging for a long period of time, its activity can also be extended to the stages of transportation and storage during product distribution.

From the point of view of food security, antimicrobial substances used in developing active packaging must be approved to be in contact with the food, and must, therefore, be considered GRAS (Generally Considered As Safe) by the FDA. In this regard, it is important to highlight that antimicrobials must be incorporated to food packaging in such concentrations so that the released concentration is allowed by the regulation.

The most commonly used food packaging antimicrobial agents are: sorbic acid, propionic acid, potassium sorbate, benzoic acid, sodium benzoate and citric acid (Quintavalla & VicinI, 2002). Bacteriocins such as raisin and pediocin have also been used (Sebti & Coma, 2002), besides other compounds, among which stand: enzymes such as peroxidase and lysozyme, the latter used to inhibit microbial growth of gram-positive bacteria (Padget et al., 1998); natural polysaccharides with antimicrobial properties as chitosan (Debeaufort et al., 1998); phenolic compounds extracted from plants; chelating agents such as ethylenediaminetetraacetic acid (EDTA), and metals, such as silver ions. More recently, triclosan compound (2,4,4'-trichloro-2'-hydroxydiphenyl ether) was approved for food contact use in the European Union by the Scientific Committee for Food (SCF, 2000) with a limit of 5 mg/kg of food.

Antimicrobial agents in packaging are able to control microbiological contamination by use of three mechanisms: reducing microorganism growth rate, increasing the lag phase, or inactivation by contact (Quintavalla & Vicini, 2002). Antimicrobials can act by inhibiting essential metabolic routes, or by intervening in the microorganism reproductive genetics, while other compounds modify the functioning of the cell membrane or the cell wall structure, as it is the case in lysozyme, which destroys the cell wall, without modifying metabolic routes, while lactoferrin and EDTA act as essential cation chelating agents (Chan et al., 2004).

Considering that most antimicrobial agents have different action mechanisms, it is considered that mixing different kinds of antimicrobial agents could increase antimicrobial activity trough synergic reactions, provided that they don't interfere with each other. Therefore, it is desirable to experiment with combinations of several antimicrobial agents, to extend its activity to a wider range of microorganisms, maximizing effectiveness and safety of packaging systems with antimicrobial agents.

Considering the method to incorporate the active agent with antimicrobial capacity to the packaging, this can be achieved in different ways. In some cases, the antimicrobial agent is incorporated as a coating in the internal part of the film which will be in direct contact with the food. Also, the antimicrobial agent can be incorporated in the polymer matrix itself, in which case, the agent diffuses through all the amorphous zones of the polymer, or through the holes and empty spaces between polymeric chains. Undoubtedly, incorporation in the polymeric matrix requires studies on the subject that define the effective concentration levels of antimicrobial agents, kinetics of the agent diffusion, distribution of the agent in the matrix and the effective action kinetics on microorganisms. On the other hand, the methodology to incorporate the active agent in the plastic film limits the possibilities to use antimicrobial agents. Thus, in case the agent is incorporated into the polymeric matrix by using extrusion, its resistance to high temperatures and high pressure becomes essential.

Active packaging technology is an emerging and promising area in food technology that can contribute with several benefits to preservation of a broad range of products. Within the concept of active packaging, antimicrobial packaging is defined as the packaging that incorporates active antimicrobial agents in its structure, avoiding addition of these substances directly on the food. The concept of antimicrobial packaging consists of gradual release of the antimicrobial agent from the package to the food, inhibiting or delaying microorganism growth on the food surface.

Active packaging application for preserving food has been used for expanding the lifespan and increasing the quality of various products such as: carrot (Villadiego, 2004), broccoli (Yamashita et 2006), strawberry (Ribeiro et al., 2007), cheese (Panuwat et al., 2007), garlic (Geraldine et al., 2008), among others.

At present, there is great international interest in the use of active packaging related to the food industry, and among them packaging with antimicrobial capacity. Nonetheless, most researches are focused on the incorporation of antimicrobial agents in non-recyclable or non-biodegradable plastic packaging, or on edible coatings applied directly on the food.

The present invention responds to development trends in technological innovations to increase productivity.

On the other hand, the globalization of international trade opens clear possibilities for the strengthening of production development and commercialization of fruit production, particularly those species recently incorporated or grown, that may become relevant in world markets, not as much due to their volume, but due to some special attributes, whether it is quality, opportunity, environmental issues or others.

In this way, quality and sustainability issues represent relatively recent concepts, which have however gained position in the consumer concern, as in authorities, producers and the academic world, among other actors in society. This new reality that has started to gradually take over the markets and production commercialization, has involved developing two basic regulatory categories: (i) those related to product quality, where regulations seek to control harmful effects, both in consumer health and the environment of the importing country, y (ii) those related to processes, where the regulations include requirements that seek to develop production processes harmless to the environment and the safety of workers in the importing countries. Added to the above is the requirement of processing techniques that can guarantee the harmlessness of the products (ODEPA, 2005).

This phenomenon, although it opens new niches in the market, such as green markets, ecological markets, environmental seals, quality certifications, among others, it is also true that it is generating new demands to industrial, agricultural, forestry and fishing production, which forces to promote a strategy based on quality, in order to broaden the access to markets and to improve competitive conditions, through technological innovation and new investments.

Today, one of the most serious environmental concerns is the amount of waste produced and stored as a consequence of packaging and boxing use. Most part of the materials used by packaging industries come from fossil fuels, which are known due to their low degradability. On account of this, food packaging materials—as any other short-term packaging material—represent a serious problem worldwide (Kirwan & Strawbridge, 2003). Thus, it is considered that 25% of world waste comes from packaging (Miltz, 2008, *Comunicación Personal*).

The current global consumption of plastic is more than 200 million tons, with an annual growth of around 5%, which represents the biggest application field of crude oil (Siracusa et al., 2008).

In the food packaging industry, to remain competitive and to offer better plastic solutions means being able of dealing with some key elements, such as the approval of food-material contact (FDA) and waste management, within most of the legislations.

Growing environmental awareness demands environment-friendly use attributes from packaging and processes. As a consequence, recyclability and/or biodegradability of packaging materials are not functional requirements, but also important environmental attributes.

The recycling of solid waste is a common practice in countries committed to sustainable development. The European Parliament and Council Directive 94/62/EC, of 20 Dec. 1994, requires for packaging and packaging waste that at least a minimum of 15% of plastic is recycled by the end of 2005, while Directive 2004/12/EC of the European Parliament and Council, of 11 Feb. of 2004 establishes that a minimum of 22.5% must be recycled by the end of 2011 (Carvalho et al., 2007).

At present there is great interest on recyclable materials, which are those materials reused by the industry in order to minimize environmental waste or even biodegradable, which are defined as those materials that degrade due to the action of microorganisms naturally present in the environment such as bacteria, fungi and algae (ASTM D6400-04). Thereby, a great effort to expand food lifespan and to improve food quality as well as reducing packaging waste have encouraged the exploration of new packaging materials.

In view of the background analyzed it becomes evident that there is enough evidence to support the possibility of using antimicrobial agents in food packaging, especially for dried fruits, in order to improve safety and harmlessness and to expand the product lifespan. Besides, the use of ecologically friendly material is a worldwide demand. However, there are no publications where the application of antimicrobial agents in industrial-level packaging is reported, especially regarding was of attaching the agent to the packaging and least of all, the use of packaging that is not only antimicrobial, but environment-friendly as well. That is the challenge of the present project: to expand the lifespan of berries through the incorporation of an antimicrobial agent to an ecologically friendly material.

Although there are few patents of antimicrobial food packaging, there are patents concerning active packaging with antioxidant capacity—not antimicrobial—but presenting microencapsulation of active agents, i.e. their incorporation in the food itself, in pharmaceutical and cosmetic products.

Particularly, USNo. 2008/0169217 shows active packaging and/or active packaging closing in different formats, made of metal and/or synthetic and/or associated natural materials where at least one element and/or component of the packaging contains and distributes one or several food additives and supplements and/or ingredients or processing aids used to produce food and cosmetics. The additive can fulfill antimicrobial functions regarding the packaged product.

WO99/49823 shows antimicrobial plastic materials such as films and meltblowing nets for food packaging wrappers, surgical covers, facial masks. What makes them similar is that they contain an agent such as methylene blue dispersed therein which generates singlet oxygen, which in turn presents antimicrobial activity. Materials can be made through cryogenic grinding, along with the substance that generates singlet oxygen, ammonium stearate or other surfactant material with properties as soup and a polymeric resin to form a consistent concentrate as a thin homogeneous powder. The concentrate is added to large batches of polymer which are then processed by conventional equipment to create plastic films, cloth, etc.

WO2004/056214 shows a preparation method for bioactive packaging materials made of synthetic polymers or polymeric materials from natural sources covering the packaging material with a polymeric coating which contains immobilized preservatives, where the application of a solution, or a polymer dispersion with preservatives in the packaging material is by means of spray and/or coating and/or sinking the packaging material in such solution or dispersion and/or fold or carving printing followed by evaporation of the solvent under room or increased temperature, and the preservative is a microbicide and/or bacteriostatic preservative and/or fungicides; antibiotics and/or silver compounds and/or phenol derivatives and/or bacteriocins and/or esters of p-hydroxybenzoic acid and/or fatty acid monoglycerides and/or benzoic acid and/or sorbic acid and/or chitosan and/or (2/4/4-trichloro-2-hydroxydiphenylether and/or lysozyme and/or nisin and/or hexamethylenetetramine.

USNo. 0220036 shows antimicrobial packaging material for food materials containing between 0.05% to 1.5% weight in an essential oil. The oil can be selected from linalool and/or methyl chavicol, but also from one or more from citral, generaniol, methyl cinnamate, methyl eugenol, 1,8-cineol, trans-a-bergamot, carvacrol and thymol mixed with one or more selected polymers of ethylene vinyl alcohol copolymer, polyacrylates, which include copolymers of ethyl acrylate, methyl methacrylate, lonomeros, nylons and other hydrophilic polymers, or polymers with functional groups capable of partly anchoring the additives, and the mixture is covered on the food contact layer of a film of food grade packaging or incorporated in a film of food grade packaging. A binding agent is added to the mixture such as polyethyleneglycol, to improve volatile oil retention in the polymer during the process. This material has no regulatory limitations and in the mentioned concentrations, it does not create detectable unwanted flavors.

U.S. Pat. No. 7,906,151 shows a cosmetic or dermatological composition comprising potassium sorbate and at least a stabilizing agent selected from microcrystalline cellulose, talc and a lipid having an interfacial tension of less than 10 mN/m.

U.S. Pat. No. 7,981,408 shows polymers for antimicrobial packaging ant their use, where the antimicrobial, such as quaternary ammonium and phosphonium salts, is covalently bonded to the polymeric material, which is used for films, food packaging, cosmetics, medical equipment and devices and others. The antimicrobial may be bactericidal, fungicidal and/or antiviral.

However, there are no documents reporting eco-active low cost packaging with easy preparation comprising a coating for the plastic packaging (PET) already formed with a preservative, especially potassium sorbate, through the immersion of the packaging already formed in a silicon-water solution containing the preservative.

As it has been said before, in recent years there has been great interest in the development of active packaging with antimicrobial capacity, to exercise this function on the food surface for as long as the food is in direct contact with the packaging. The packaging materials with antimicrobial characteristics can be divided in two major groups: those which possess antimicrobial agents that must migrate to the surface of the packaging to exercise their function and that come into direct contact with the food, or those which do not require to migrate to exercise their function. Various films with antimicrobial characteristics have been developed, manly in Japan. Thus, Dupont has introduced MicroFree™, based on the incorporation of three kinds of silver or copper salts on a support of inorganic powder, thermosetting agents and which can therefore be introduced in the polymeric resin itself during the extrusion process.

At present, three kinds of MicroFree™ are being offered: Z-200 (silver on a zinc support), T-558 (silver, copper oxide and zinc silicate on a titanium dioxide support), and B-558 (silver, copper oxide and zinc silicate on a barium sulphate support), which have proved to have a beneficial effect on *Escherichia coli, Ps aeruginosa, Kb pneumoniae* y *St aureus*. These agents, in spite of being approved by the EPA (Environmental Protection Agency), have not been approved by the FDA for direct contact with food. Metallic ions, copper and silver, as well as quaternary ammonium salts and other compounds, are allowed in Japan, but not in the US as safe antimicrobial agents.

For their application in food packaging these agents not only must be safe, but they must also migrate with difficulty towards the food. Although copper ions can destroy microorganisms and viruses and the fact that copper is essential for life, being an enzyme constituent, it is considered toxic and it is not allowed by the American regulation for direct contact with food.

As it was mentioned earlier, In Japan regulations for the use of metallic ions are not as strict as they are in the US, and for that reason there has been plenty of work on the incorporation of silver ions, inert supports such as synthetic zeolites in many cases (type minerals: $xMn_2O.Al_2O_3.ySiO_2.zH_2O$), such as the Apacider A™ in which the silver ions chemically and physically bind with calcium phosphate on a zeolite support. Nevertheless, this agent presents problems in its incorporation as extrusion additive, requiring a large number of surfactants that must be added both during the extrusion process, to thereby enhance its dispersion in the plastic matrix and its migration towards the food service. The company Japan's Shinanen New Ceramics along with Mitsubishi, developed the Zeomic™ where they incorporate silver ions on a zeolite support. With a broad range of action. Although showing good performance in the extrusion process, restrictions for its use remain, due to incompatibility for direct food contact.

Other compounds have been proposed and their antimicrobial capacity has been evaluated. For example, antimicrobial Microban™ (5-chloro-2-(2,4 dichlorophenoxy) phenol) can be found in the market, and it is widely used in polyolefins with applications in toys, garbage bags, cuffing boards for kitchen, among others. However, it has to be mentioned that Microban is not accepted by the American regulation as a material for direct contact with food, and it is even being questioned by the EPA. Japanese company Sumimoto developed a thermoplastic resin for food packaging films, incorporating benomyl, one of the systemic fungicides with the broadest range of action; however, it is highly improbable that US regulating authorities accept benomyl for direct contact with food.

Some other structures with antimicrobial characteristics refer to the formation of chlorine dioxide inside the packaging. This invention by the Southwest Research Institute and Bertrand Technologies, Inc. has led to the packaging system called Microatmosphere™, where the use of chlorine dioxide for food packaging has been accepted in the US.

There are many efforts being made in the search of active agents from natural sources with antimicrobial capacity, many of which are being tested for their effectiveness in Vitro in laboratory experiments; however, there is a lack of technological development to be able to apply these agents in food packaging processes, and that is what will be addressed by this patent by means of the extrusion process or coating.

The incorporation of antimicrobial agents both inside the polymer matrix and in the form of coating must meet the international legislation concerning packaging materials to be in direct contact with food. For instance, the US legislation defines a food additive as any substance which under use conditions may become part of the food, so all those components which intentionally or non-intentionally, may pass to the food from the packaging material must be previously admitted as food additive, except for substances recognized as GRAS (title 21 of the of Federal Regulations). Therefore, in this case the antimicrobials to be incorporated in the structure must be approved for their use in direct contact with food by the FDA, or they must be GRAS substances, as it is the case of natural origin substances (plant extracts such as thymol, carvacrol, linalool, among others). In the case of using antimicrobials approved by the FDA, the legislation requires levels of maximum global migration of the extractable substances from the packaging material.

These regulations and requirements concerning food packaging material are included in the form of positive lists in the Code of Federal Regulations (CFR), in parts 174-179. The regulations are subdivided in sections for polymers, adhesives, coatings, adjuvants, among others, thus establishing the additive identity, safety conditions for its use and, in the case of polymer resins, they specify limits of all extractable substances of the finished article.

The present invention refers to additives included in FDA positive lists and with GRAS agents. Alongside, it has been considered the use of plastic packaging with high permeability to oxygen, as it is required in American legislation in order to avoid anaerobic bacterial growth (antibioterrorist legislation www.fda.gov).

The European Union has a very strict regulation on the necessary characteristics of packaging that is in direct contact with food, so that packaging must be ruled by Directive 2005/79/EC of 18 Nov. 2005, which rules all, aspects concerning articles and materials which are in direct contact with food, and where the limits of maximum global migration (i.e. total amount of components that can pass from the packaging into the food, regardless of their nature) and specific migration (maximum amount of a specific component that can pass from the packaging into the food, subject which has a particular interest from the toxicological or sensorial point of view) for the starting substances and additives used when manufacturing plastic materials for food.

Nonetheless, European legislation in Regulation 1935/12004 authorizes two kinds of packaging: one that reacts "intelligently" on the product by indicating if the product has expired or is degraded, and another one that reacts "actively" by introducing beneficial chemical modifications in food, which increases its storage time. This Regulation is consistent with the latest developments in the food-packaging innovation area. In any case, the incorporation of antimicrobial agents will be performed according to and following international legislation.

When discarded, food packaging can become the most evident waste source produced by the public. This has raised environmental concerns, leading to a strengthening of European legislation (Packaging and waste—Directive (94/62/EEC)) and Boxing Regulation (Essential Requirements, 2003), in order to reduce the amount of packaging waste, in this way, solid waste recycling is common practice in those countries committed to sustainable development. The European Parliament and Council Directive 94/62/EC of 20 Dec. 1994, requires for packaging and packaging waste that a minimum of 15% plastic is recycled by the end of 2005, whereas Directive 2004/12/EC of the European Parliament and of the Council of 11 Feb. 2004 states that a minimum of 22.5% must be recycled by the end of 2011.

Undoubtedly, the present invention addresses directly reduction of the impact on the environment caused by traditional packaging waste. Whereas berries are currently commercialized in primary packaging made of non-biodegradable polymeric materials which produce environmental contamination after its use changing that kind of packaging for recyclable and/or biodegradable packaging, more according to international regulation requirements 2005/20/EC and to consumer requirement internationally, will lead to the fulfillment of such requirements. Therefore, the present invention represents a beneficial environmental impact.

There is still need to consolidate or improve the presence of food stuff in highly demanding markets, a goal that can be achieved as long as the food, besides being competitive an attractive, is safe, good quality and with a lifespan appropriate to the distance it is sought to bridge. Thus, it is required to develop food preserving technologies where the packaging systems play an essential role in expanding the lifespan, increasing the quality and safety of the food, incorporating in this way added value to the product.

To be a leader in the food industry, it is necessary not only to be a leader in the production and exporting area, but also in innovation and Development of packaging systems capable of safeguard the quality of food, with special attention on consumer requirements worldwide. Thus, one of the requirements in developed countries—where consumers are highly aware of the environmental damage that packaging waste produces—is linked to environment-friendly packaging, an area in which biodegradable and/or recyclable packaging have a very important part.

It is possible to develop totally recyclable or biodegradable packaging with antimicrobial capacity to inhibit microbiological growth on the surface of the packaged product, to be able to offer safer food, with better quality and a longer lifespan, reducing loss and rejections of fresh refrigerated fruits. This innovation will also allow to reach new markets which require increasingly environment-friendly packaging.

The combination of the active function of the packaging and its positive impact on the environment is what makes the present invention different. The packaging incorporates a proactive and positive aptitude on the packaged food, combining the antimicrobial activity with the reduction of the environmental impact. Thus, a solution easy to be adopted by the industry can be obtained.

SUMMARY

The present invention proposes a packaging that besides expanding the lifespan of berries, due to the incorporation of an active agent with antifungal capacity on the surface of the package itself, so that during the time the fruit is packaged an antifungal effect is permanently exercised on the surface (the place where most of the deterioration processes occur), it is also capable of contributing to the preservation of the environment. It also proposes a procedure for its preparation and use.

The main component of the present invention is the incorporation of antifungal agents to recyclable materials for the development of active packaging with positive environmental impact (eco-active) which allows to expand the lifespan of fresh berries.

In the present invention an antimicrobial agent has been selected, effective against fungi, especially *Botrytis*; a minimum inhibitory concentration of this compound is indicated; the ecological correct material is selected; the antifungal material is incorporated to recyclable materials and the lifespan of the product in the new packaging is determined according to its microbiological characteristics.

Microorganism growth, especially of fungi such as *Botrytis cinerea*, is the limiting factor of the lifespan of fresh berries. The negative impact of packaging is a world concern and consumers increasingly demand environment-friendly packaging. Therefore, if berries are packaged in active recyclable and/or biodegradable packaging which have the capacity to reduce microorganism growth, the lifespan of the product can be expanded and the problem of packaging waste in the environment minimized.

By having semi-rigid containers with capacity to inhibit *Botrytis* growth that are also environment-friendly the lifespan of refrigerated fresh berries packaged with these materials will be expanded. It is possible to develop an active environment-friendly packaging which may allow to increase in at least 30% the lifespan of fresh berries, at competitive costs, compared to traditional packaging used by berry exporting industries, without modifying the current packaging production line.

The material developed in the present invention is a berry packaging which allows to have a product with a longer lifespan, according to the requirements of the destination market, increasing the capacity to obtain berry supplies from more distant places. By extending the lifespan of berries it will be possible to reach more distant and more environmentally aware markets, thanks to substitution of conventional plastics packaging, which causes negative impact in the environment.

The present packaging allows the commercialization of berries to obtain better economic results, to expand the lifespan of fruit at a competitive cost compared to traditional packaging, with the advantage of being environment-friendly and without demanding transformations in the current packaging production line.

BRIEF DESCRIPTION OF THE DRAWINGS

FIG. 1—Addition of the silicone solution in water, incorporating the antifungal agent to the packaging production line (A). RPET sheet extruded, receiving solution coating (B).

DETAILED DESCRIPTION

The present invention comes from the application of Polyethylene terephthalate (PET), 100% recyclable, known as RPET. It was chosen because it is the most widely used in more than 90% of the fruit industry for its features concerning cost, transparency and resistance. It is also a material that can be reused and recycled.

The antifungal agent initially tested in this invention was potassium sorbate, due to its effectiveness against fungi especially *Botrytis cinerea*, because of its GRAS character (Generally Recognized As Safe) and for being used directly on foodstuff.

The manufacturing process of the active antifungal packaging does not interfere with the elaboration process of conventional packaging. This invention uses a bath of water plus silicone, usually used by PET thermo forming enterprises in order to prevent the packaging from sticking together when being stacked. In the industrial process, once the extruded PET film is immersed in the silicone containing bath, then immediately the excess of solution is removed and the film rolled to later continue to the thermoforming and production process of the packaging.

Figure 1A:
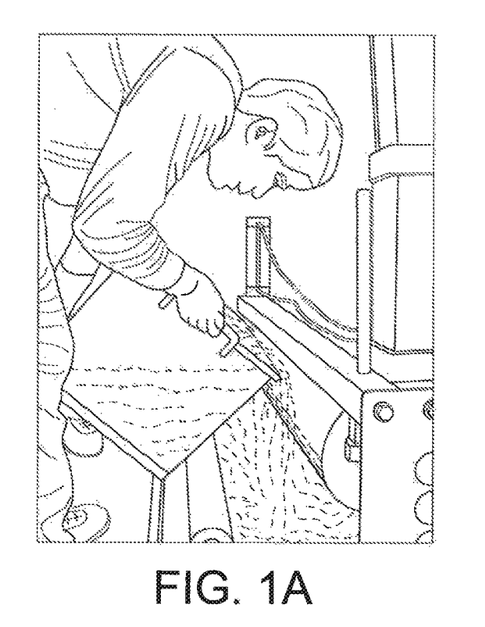

In order to produce the active container, the silicone bath was used to incorporate the antifungal agent (potassium sorbate) which is chemically soluble in water and silicone, forming a homogeneous solution (FIG. 1A)

Figure 1B:
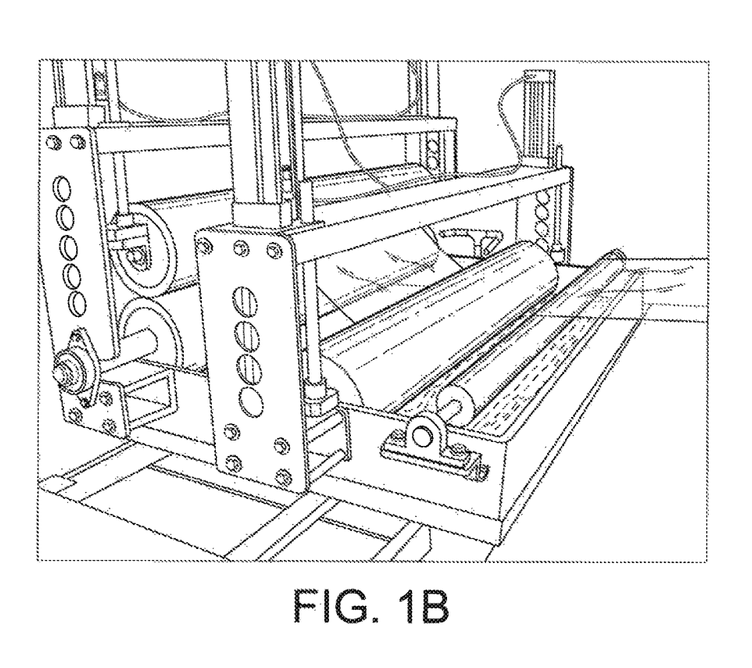
Figure 2:
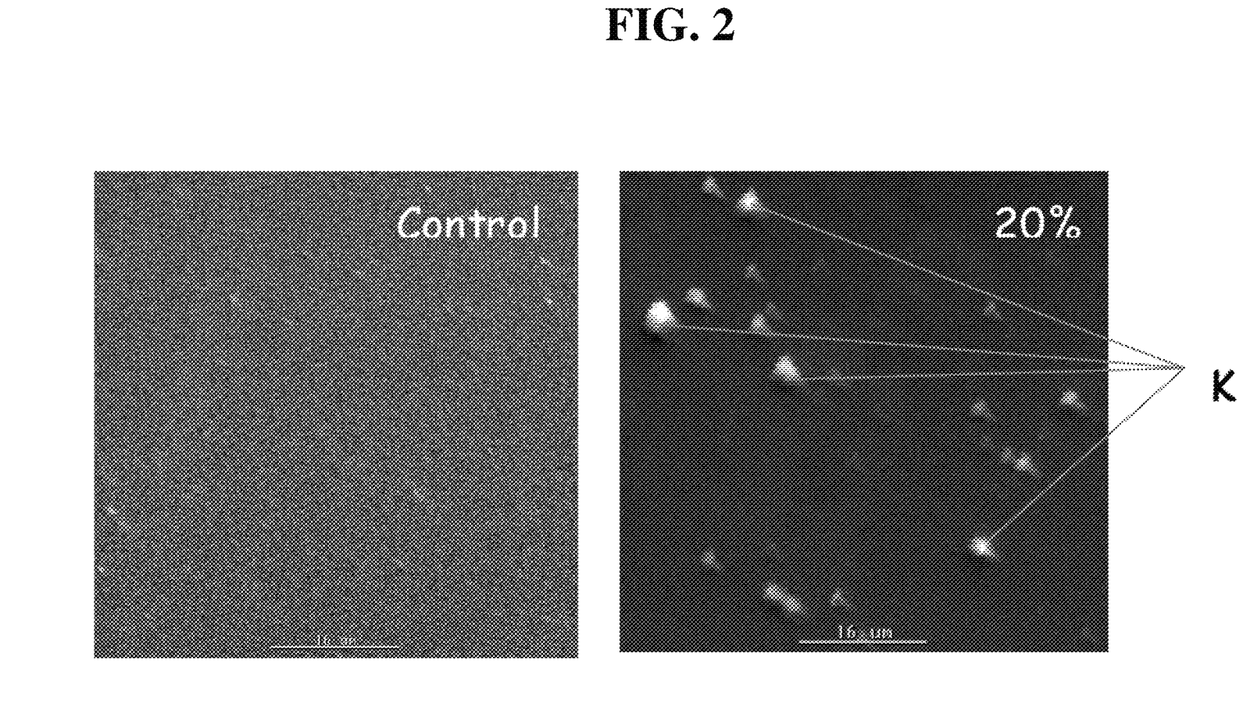
FIG. 2—Shows SEM images of the PET+Antifungal B (potassium sorbate) film.

Thus, when the RPET film passes through the silicon bath it is also impregnated with an antifungal agent (FIG. 1B), that was "trapped" by the silicone deposited on the surface. FIG. 2 (image scanning electron microscopy, SEM) shows the presence of potassium the polymer surface.

As the antifungal agent used withstands temperatures up to 270° C., the thermoforming process (±140° C.) does not affect its stability.

Laboratory studies using liquid chromatography (HPLC) showed that about 0.1% of the antifungal agent added to the bath is adhered t the packaging (for a silicone bath containing between 18-20% w/v of antifungal agent in the silicone solution in water).

Study of Minimum Inhibitory Concentration (MIC)

Studies on the minimum inhibitory concentration of potassium sorbate against *B. cinerea* were performed using potato dextrose agar, containing 10 concentrations of the antifungal agent, ranging from 0.0 to 1.0% w/v (antifungal agent in silicone solution in water) for an initial concentration of *B. cinerea* of $10^5$ cfu/mL and from 0.0 to 0.2% w/v, for to an initial concentration of *B. cinerea* of $10^3$ cfu/mL. At the center of the plates 30 μL of a suspension containing $10^5$ to $10^3$ cfu/mL of spores of *B. cinerea* were incorporated, with 5 days of growth at 25° C. The plates were incubated at 25° C. for 5 days and then growth in various concentrations was observed.

Figure 3:
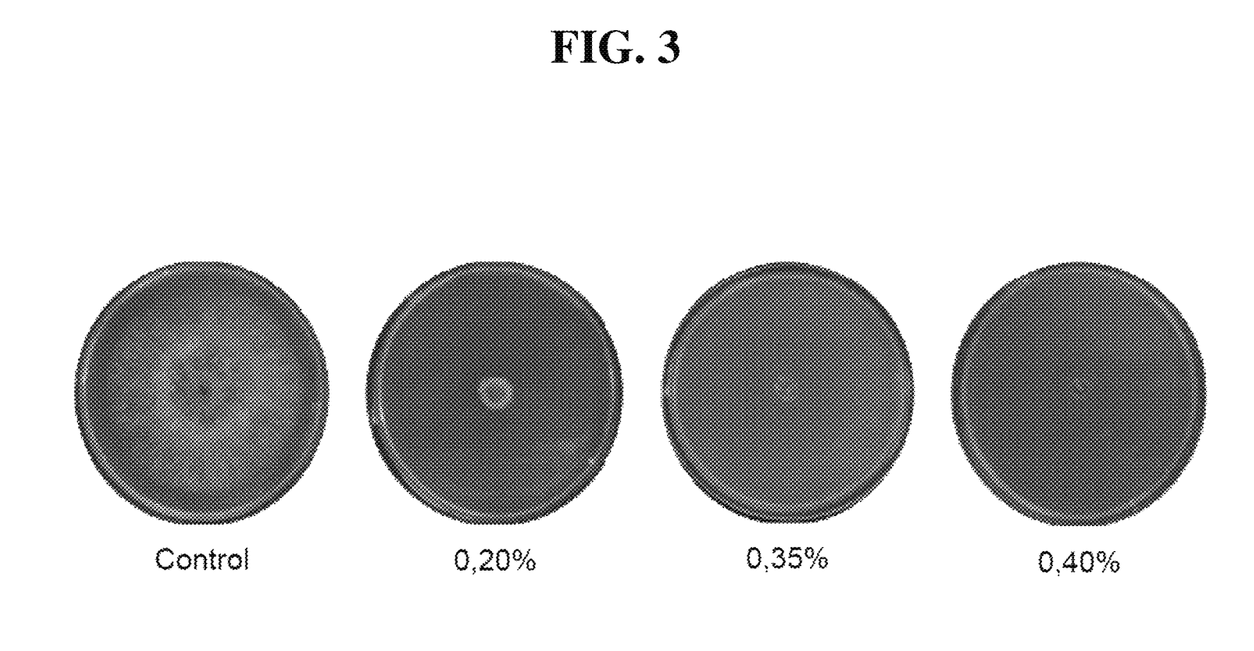
FIG. 3—Potassium sorbate CMI for an initial concentration of *B. cinerea* of 105 cfu/mL.
Figure 4:
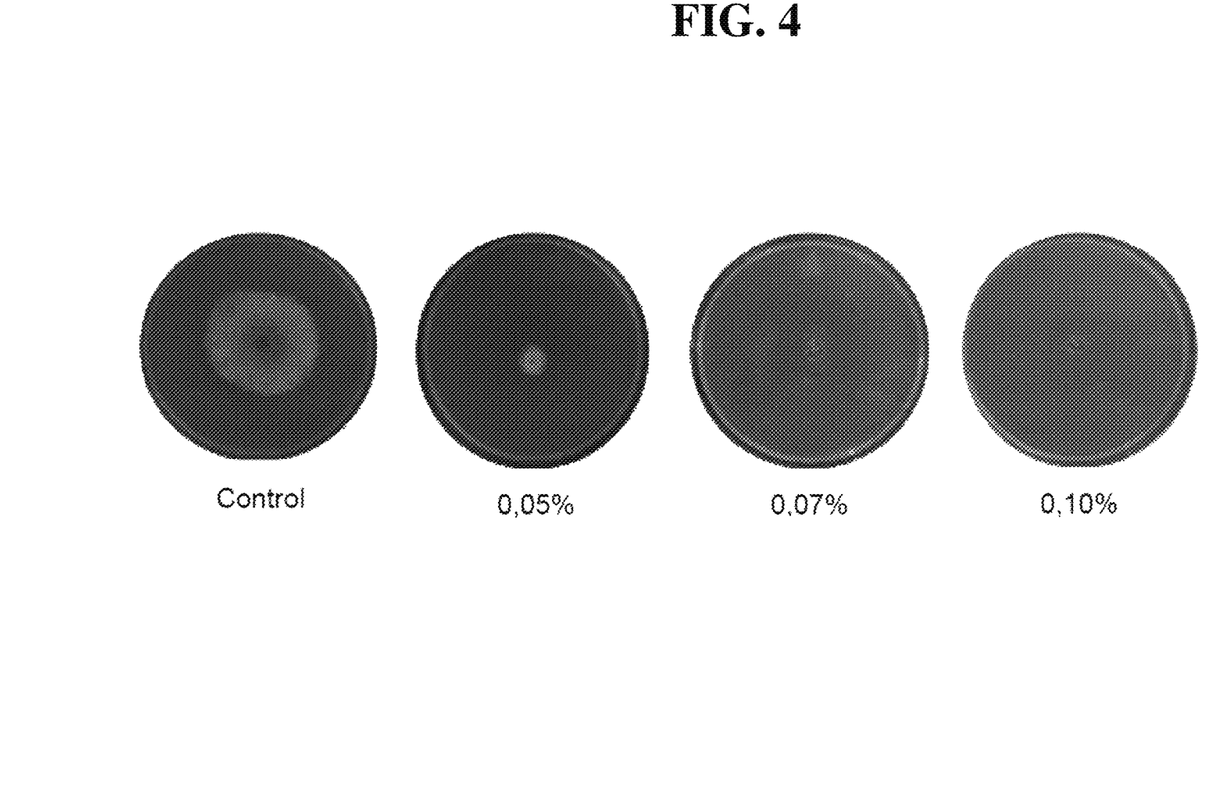
FIG. 4—WCC potassium sorbate to an initial concentration of *B. cinerea* of 103 cfu/mL.

For a concentration of $10^5$ cfu/mL of *B. cinerea*, the minimum inhibitory concentration of potassium sorbate is between 0.38 and 0.40% w/v (FIG. 3). For $10^3$ cfu/mL (closest counting to that observed in the fruit export) minimum inhibitory concentration is between 0.07 and 0.10% w/v (FIG. 4).

Figure 5:
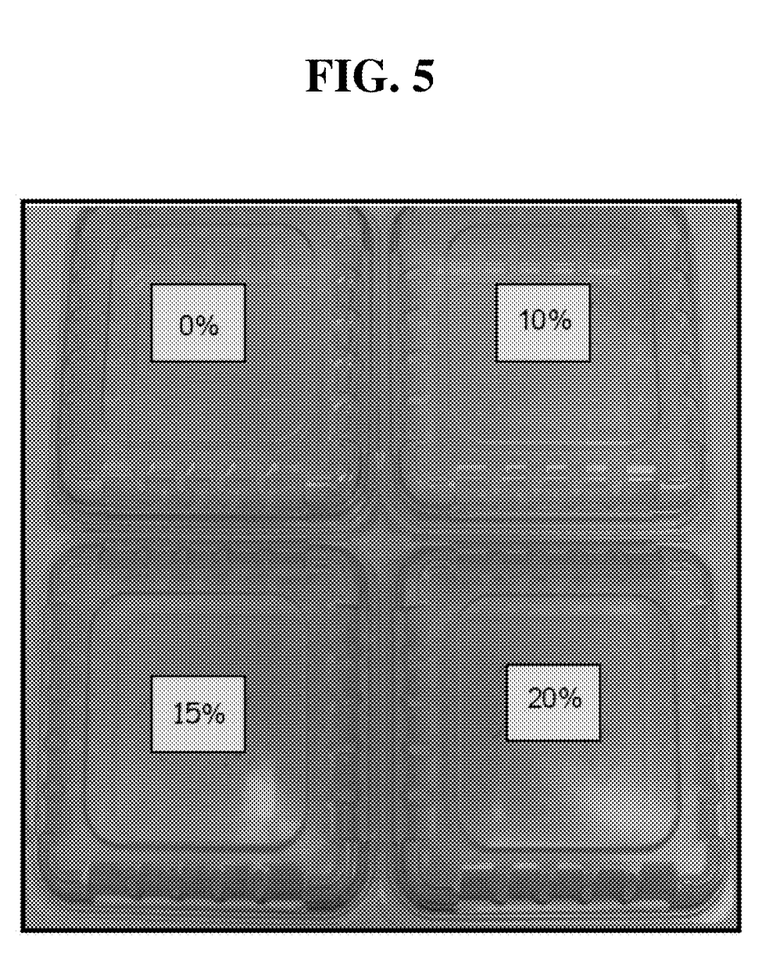
FIG. 5—Shows the result of the whole process (Coating and Thermoforming) at pilot level. Antifungal potassium sorbate.

At a pilot scale packaging was produced with respective concentrations of antifungal agent: 0.0 (control), 10.0, 15.0 and 20.0% w/v (FIG. 5).

Study of the Eco-Efficiency Active Package Against *B. cinerea*

Studies on the efficiency of produced eco-active packaging against *B. cinerea* were based on the Halo Test, using potato dextrose agar. At the center of the plates 30 μL of a suspension containing $10^5$ cfu/mL of spores of *B. cinerea* were incorporated, with 5 days of growth at 25° C. and, at equidistant positions at the ends of the plate four packaging discs were placed with 1 cm diameter. The plates were incubated at 25° C. for 5 days and then growth of fungi in different concentrations of antifungal incorporated into the package was observed.

Figure 6:
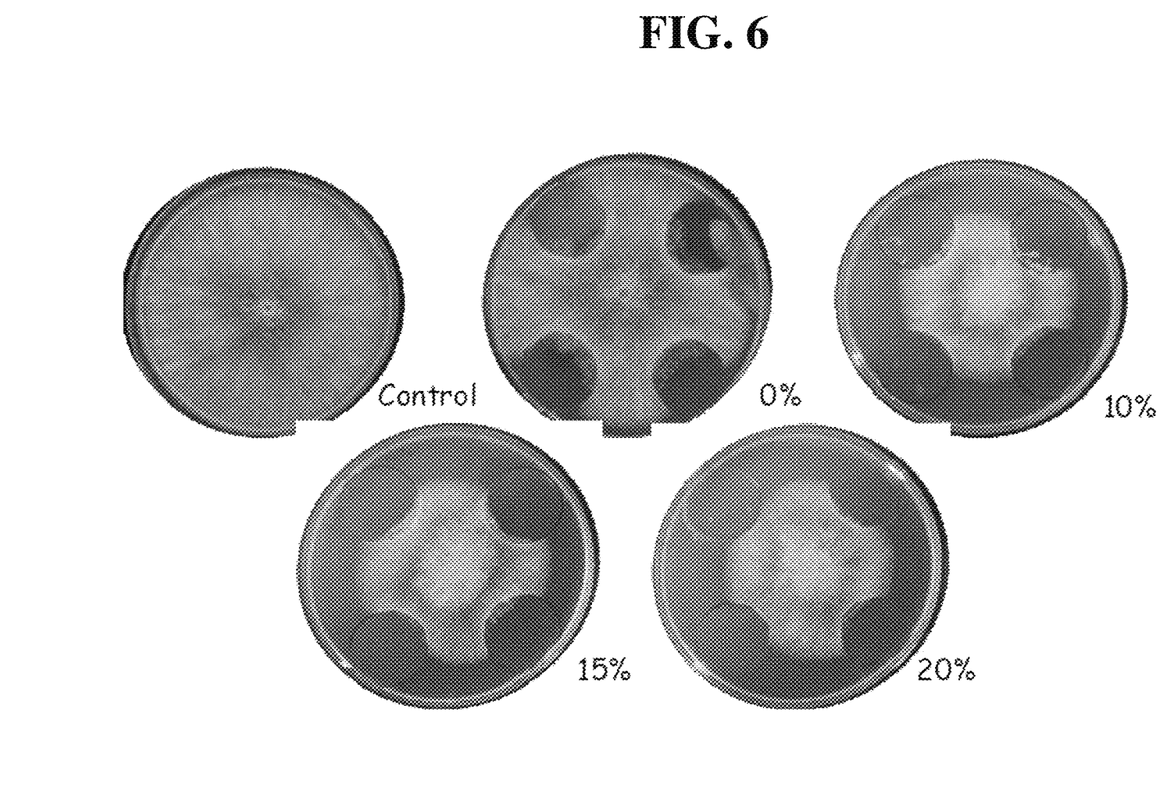
FIG. 6—Shows the Halo test in pilot-scale prototypes. Initial concentration of *B. cinerea*: $10^5$ cfu/mL. The plates were incubated for 5 days at 25° C. The assay was performed in duplicate, with 4 repetitions.

Halo tests demonstrate the effectiveness of the films produced at different concentrations, against *B. cinerea*. Assays were performed in triplicate with three repetitions (FIG. 6).

Figure 7:
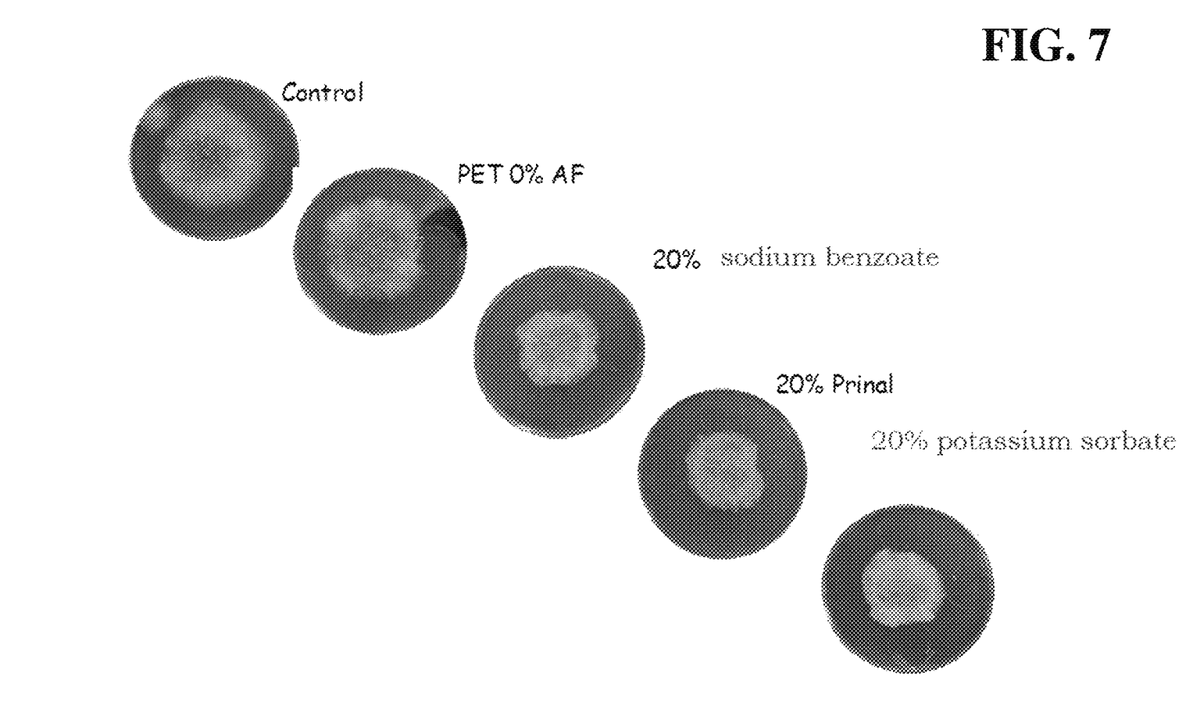
FIG. 7—Sample test Halo—Coating. Initial concentration of *B. cinerea*: $10^5$ cfu/mL. The plates were incubated for 5 days at 25° C. The assay was performed in triplicate, with 3 repetitions.

Sodium benzoate was studied as an alternative antifungal and also the mixture of potassium sorbate plus sodium benzoate (commercially prepared for direct use in food) to verify the cost/benefit for the preparation of the final packaging (FIG. 7). Assays were performed in triplicate, with 3 repetitions.

Study of the Efficiency of Eco-Active Packaging Containing Blueberries.

Figure 8:
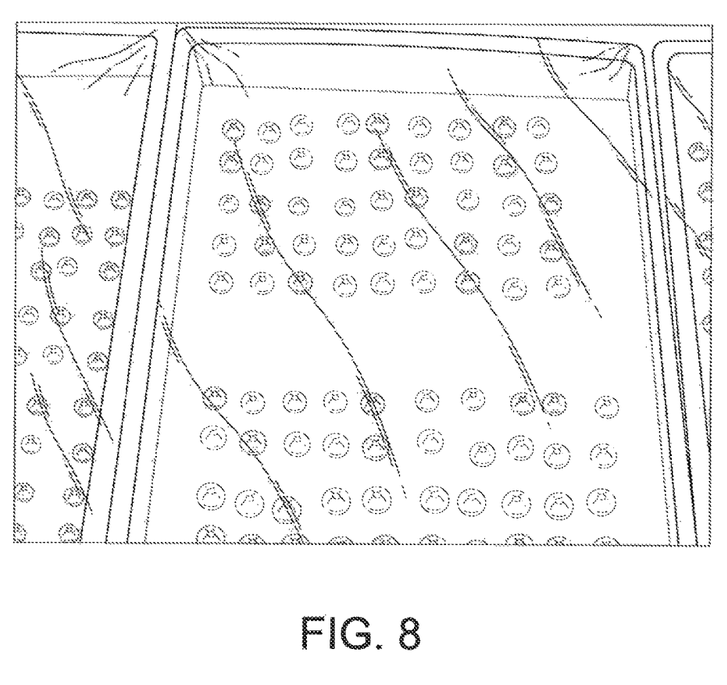
FIG. 8—View of blueberries in a moist chamber.

This test consisted in determining contamination postharvest fungus making a count of the total number of fruits in the wells in blueberry fruit for export from two producers from different regions in the country identified as A (Town of Panguipulli, Province of Valdivia, Los Ríos Region) and B (Town Collipulli Malleco Province, Araucanía Region). The treatments the fruit was subject of were two storage temperatures, 4 and 10° C., cold room with 85% humidity and two types of packaging, conventional (RPET) and active (RPET with addition of 20% potassium sorbate antifungal agent), with 11 repetitions (each consisting of a cup of 125 gr) and 5 evaluation dates (0, 7, 14, 21 and 28 days). The experimental design was completely randomized. When establishing the assay, the initial contamination of fruit was determined by visual observation of all fruit from 10 wells, as well as 400 fruits that were subject of favorable conditions for developing postharvest pathogen agents, i.e. moist chamber on plastic trays with humid paper towel and covered with plastic for 7 days (FIG. 8).

Figure 9:
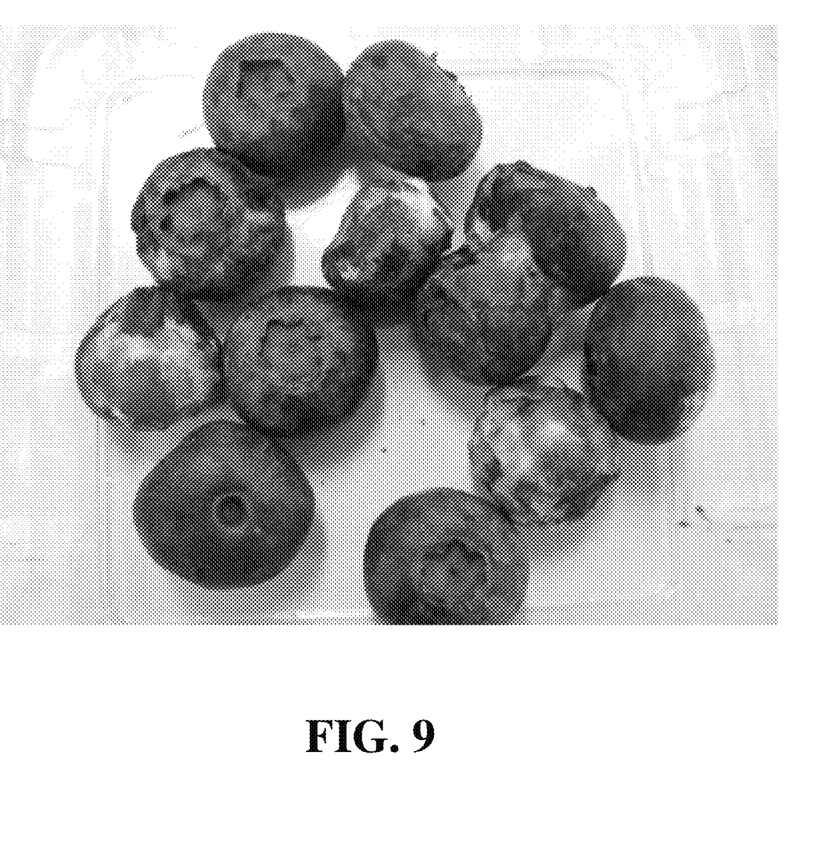
FIG. 9—Cranberry fruit with *Borryris cinerea* mycelium.

Once finished the time of permanence in storage conditions for each evaluation date, the fruit was removed from the cold room and assessed in the phytopathology laboratory, making a count of the total number of fruits in the wells, and separating the number of fruits contaminated with *Botrytis cinerea* (FIG. 9), visually or with the aid of a stereomicroscope. Then the percentage of infection in each treatment was calculated. These values were statistically analyzed, transforming the data previously to $\sqrt{n+0.5}$. LSD test was used to separate the significance between means, considering $p \leq 0.05$.

At the beginning of the assay no visual differences were observed concerning the health of fruits from both producers, but in cold room after 5 days a slight difference was observed, where producer A had 1.25% of contamination by *B. cinerea* and producer B a 3%.

The results for the different dates of assessment according to the statistical analysis and the evaluated parameters are indicated in Table 1 which shows that for producer A (very healthy fruits) differences were found starting from the evaluation of 21 days of storage and temperature, not for the kind of packaging. While for producer B, from day 7 of storage, there was an effect of temperature on the contamination of fruits by the fungus. Differences were also found for the type of container at 21 and 28 days and interaction between the two factors in two evaluation dates.

TABLE 1

Effect of different factors on contamination of *Botrytis cinerea* in blueberries from two producers, statistical analysis results.

| Parameter | Producer A % of *B. cinerea* on different evaluation dates | | | Producer B % of *B. cinerea* on different evaluation dates | | |
|---|---|---|---|---|---|---|
| | 4 | 1 | 8 | 4 | 1 | 8 |
| Temperature | S | S | * | * | * | * | * |
| Packaging | S | S | S | S | S | S | * | * |
| Temperature* packaging | S | S | S | S | * | S | S | * |

NS = not statistically significant values according to LSD test P ≤ 0.05
** = Statistically different values according to LSD test P ≤ 0.05

In tables 2 and 3 results for *Botrytis cinerea* contamination by type of container for different sampling dates are shown. It is observed that the producer A had no effect of the type of packaging on contamination and that it was very low, not even 1% most of the time. For the fruit from producer B, who had larger contamination, a positive and promising effect of the packaging was observed, especially at 21 and 28 days of storage.

TABLE 2

Percentage of contamination of blueberry fruits from producer A by *B. cinerea* in different packaging.

| | Producer A % *B. cinerea* at different days of evaluation | | | |
|---|---|---|---|---|
| Packaging | 7 | 14 | 21 | 28 |
| Active | 0.10* a | 0.05* a | 2.64* a | 0.43* a |
| Conventional | 0.06 a | 0.2 a | 2.32 a | 0.62 a |

Values with different letters in each column are statistically different according to LSD test P≤0.05.

TABLE 3

Percentage of contamination of blueberry fruits from producer B by *B. cinerea* in different packaging.

| | Producer B % *B. cinerea* at different days of evaluation | | | |
|---|---|---|---|---|
| Packaging | 7 | 14 | 21 | 28 |
| Active | 0.11* a | 3.43* a | 5.25* b | 12.13* b |
| Conventional | 1.02 a | 5.22 a | 7.69 a | 17.85 a |

Values with different letters in each column are statistically different according to LSD test P≤0.05.

The results concluded that the health of the fruit when the test set was crucial in the results obtained.

The fruit from producer A developed very low percentages of infection by *B. cinerea* during the entire evaluation period, so that no differences between treatments were determined.

It was found that the fruit from producer B had larger contamination by *B. cinerea* as well as a positive effect of the active packaging, by reducing contamination by fungus, especially on days 21 and 28 of storage.

The invention claimed is:

1. A process for making a package of polyethylene terephtbalate (PET) with an antifungal agent incorporated into its surface, the method comprising:
   a) adding to a mixture of silicone in water, the antifungal agent in an amount less than or equal to 20% w/v and thereby forming a homogeneous solution as bath; and
   b) immersing in said bath extruded PET sheets and subsequently performing the steps of thermoforming and producing the final package.

2. The process of claim 1, wherein less than 15% w/v of the antifungal agent is added in the silicone solution in water.

3. The process of claim 2, wherein less than 10% w/v of the antifungal agent is added in the silicone solution in water.

4. The process of claim 1, wherein the extruded PET sheets, are immersed in a bath of silicone in water containing 18-20% w/v of antifungal.

5. The process of claim 1, wherein the antifungal is an antifungal against *Botrytis cinerea*.

6. The process of claim 1, wherein the antifungal agent is potassium sorbate.

7. The process of claim 1, wherein the extruded PET sheets are sheets of recycled PET.

* * * * *